(12) United States Patent
Oreja Puerto et al.

(10) Patent No.: US 8,814,813 B2
(45) Date of Patent: Aug. 26, 2014

(54) CRANIAL DEVICE WITH ROTARY TILT SENSOR

(75) Inventors: Daniel Oreja Puerto, Sant Antoni de Vilamajor (ES); Jordi Rigau Rigau, Barcelona (ES); Joaquin Jose Duran Cantolla, Vitoria-Gazteiz (ES)

(73) Assignees: Sibel, S.A., Barcelona (ES); Administracion General de la Comunidad Autonoma de Euskadi, Vitoria-Gazteiz (ES)

( * ) Notice: Subject to any disclaimer, the term of this patent is extended or adjusted under 35 U.S.C. 154(b) by 559 days.

(21) Appl. No.: 13/254,340

(22) PCT Filed: Feb. 26, 2010

(86) PCT No.: PCT/ES2010/070108
§ 371 (c)(1),
(2), (4) Date: Nov. 14, 2011

(87) PCT Pub. No.: WO2010/100307
PCT Pub. Date: Sep. 10, 2010

(65) Prior Publication Data
US 2012/0071798 A1    Mar. 22, 2012

(30) Foreign Application Priority Data
Mar. 2, 2009 (ES) .................. 200900451

(51) Int. Cl.
*A61H 11/00* (2006.01)
*A61F 5/56* (2006.01)

(52) U.S. Cl.
CPC ....................................... *A61F 5/56* (2013.01)

USPC .................. 601/71; 601/46; 601/67; 601/69; 340/407.1

(58) Field of Classification Search
USPC ................. 601/46, 49, 50, 53, 60–61, 65–67, 601/69–71, 74; 340/407.1, 575, 573.7
See application file for complete search history.

(56) References Cited

U.S. PATENT DOCUMENTS

| | | | |
|---|---|---|---|
| 4,938,476 A | 7/1990 | Brunelle et al. |
| 5,081,447 A | 1/1992 | Echols |
| 5,458,105 A | 10/1995 | Taylor et al. |
| 6,057,767 A | 5/2000 | Barnoach |

OTHER PUBLICATIONS

International Search Report for PCT International Application No. PCT/ES2010/070108 completed Jun. 10, 2010.

*Primary Examiner* — Tatyana Zalukaeva
*Assistant Examiner* — Kathrynn Reilly
(74) *Attorney, Agent, or Firm* — Barnes & Thornburg LLP

(57) ABSTRACT

The invention relates to an improved cranial device with a rotary inclination detector, including a container box which can be secured to the cranium of sleeping person and which contains an electric motor and an eccentric counterweight coupled thereto, forming a vibrator. The device also includes a battery or a battery holder for at least one battery, which is provided with two axially opposed projecting contacts or studs. The container box is provided with inclined formations with dielectric properties, on which the battery or battery holder can roll by means of the studs thereof, and two electric contacts on which the inclined formations terminate, such that, when the battery holder is placed on the electric contacts, the motor circuit is closed, thereby activating the vibrator.

8 Claims, 1 Drawing Sheet

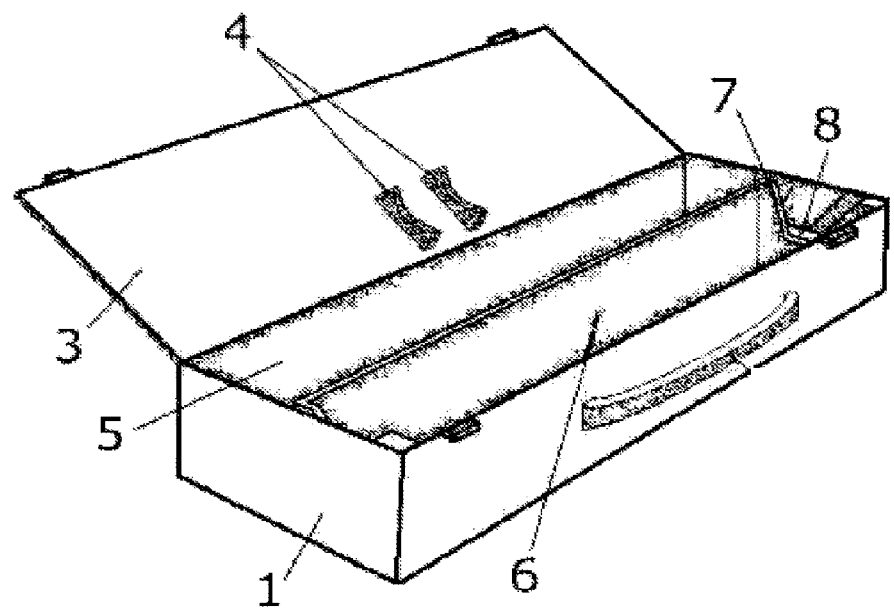
FIG. 1
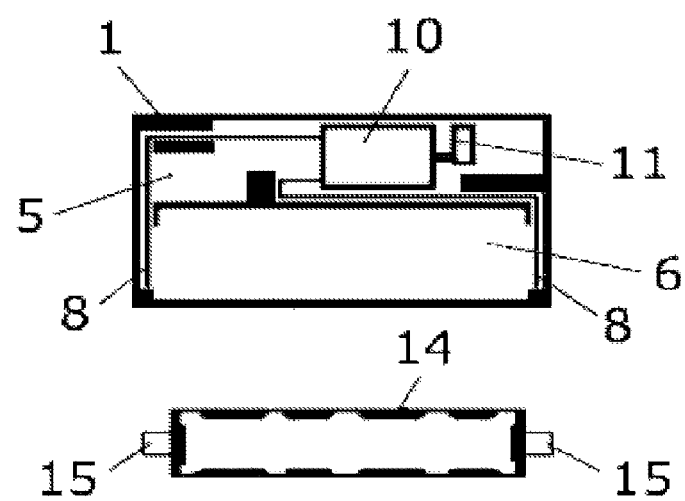
FIG. 2A
FIG. 2B

CRANIAL DEVICE WITH ROTARY TILT SENSOR

CROSS-REFERENCE TO RELATED APPLICATIONS

This application is a U.S. national counterpart application, filed under 35 U.S.C. §371, of International Application Ser. No. PCT/ES2010/070108 filed Feb. 26, 2010, which claims priority to Spanish Patent Application Ser. No. P200900451 filed Mar. 2, 2009, the disclosures of both of which applications are hereby incorporated herein by reference in their entirety.

OBJECT OF THE INVENTION

The present invention relates to a cranial device with rotary tilt sensor for preventing the respiratory obstruction during sleep, comprising a container box that can be attached to the skull of the sleeper and, arranged inside said box, an electric motor and an eccentric counterweight coupled thereto, with which it forms a vibrator.

The object of the present invention application is to provide a skull-attachable device with a detection mechanism of the supine decubitus posture and deterrent by means of vibration, with the purpose of being utilized by a person prone to respiratory obstruction or resistance while sleeping and which frequently end up in snore or respiratory apneas during sleep.

The supine decubitus posture during sleep is the one that brings about more obstruction in the respiratory passages, by the tongue falling backwards and greater relaxation of the throat musculature, making contact or pressing in excess against other related organs or tissues. This occurs by the muscle tonicity in the deep sleep phase being reduced and by the effect of gravity, which produces a partial or total blockage at the level of the Rhino-pharynx or the Oro-pharynx, increasing during inhalation the negative pressure at the narrowest point by the air flow having to pass more forced. Accordingly, suction and unconscious vibration of the surrounding tissues accompanied by snoring or temporary respiratory arrest is produced.

When sleeping with the device, the user should stay in a side decubitus posture counteracting the "plug" effect, and being aware of maintaining this posture during sleep in order to not activate the vibrator, since it transmits an uncomfortable and annoying rattle to the skull. This effect results, at the same time, totally innocuous to the user.

BACKGROUND OF THE INVENTION

Until now, cranial devices with the system of the present application are not known. Indeed systems as a backpack for the back exist, resulting harmful to health because they reduce the blood supply to the arms, due to the fit of its harness which combined with the natural movements when sleeping acts as a tourniquet. Also, containers with objects similar to tennis balls attached to the back of the pajama are utilized, altogether resulting insufficient and with the drawback of having to sleep with upper garment during the summer, and the effect of interfering with the quality and quantity of sleep. Indeed two Utility Models exist similar to the applied for, the titles of which are "Disuasor Postural durante el sueño" (Postural deterrent during sleep) with Application No. U 200601677 and publication number ES 1063432U and "Dispositivo craneal perfeccionado para disuación postural durante el sueño" (Perfected cranial device for postural deterrent during sleep) with application No. U 200702433 and publication number ES1066861U, but lacking the tilt sensor system which is described in the present specification, the programmable delay circuit, the circuit for progressive increase of intensity, memory and connectivity.

DESCRIPTION OF THE INVENTION

The invention object of the present invention is consisting of two pieces coupled to each other as a container box, and with means for attaching to a textile tape allowing it to conform to the skull of the user, being able to be positioned on the forehead. Inside the box, some means for producing vibration are housed holding thereto. Inside the same container box, the feed system based on power cell or rechargeable battery is placed, also some means for activation of the means of vibration are placed, which are activated when the individual over whom the postural sensor is arranged, adopts a certain position.

The activating means of the means of vibration can be:
rotary means, i.e. acting by rotation, and which at the same time can be
a power cell holder, which houses one power cell, and wherein the power cell holder has some contacts, overhanging or lugs, at their axially opposed ends.
a conductive metal cylinder
These rotary means work in collaboration with the shape of the container box which presents at its ends some tilted structures with dielectric characteristics over which the rotary means can roll through their ends until making contact with two electrical contacts wherein said tilted structures terminate.
a conductive metal sphere, housed in a conic-shaped conductive bush as a funnel with the suitable tilt and with a contact separated by a dielectric placed in the opening of smaller diameter of the mentioned conical bush, such that by horizontally positioning the assembly, the sphere is displaced over the wall of the conical bush by gravitational effect, until coming to rest over the bottom contact, closing the electrical circuit and activating the vibrator.

The mentioned three types of rotary means for activation, are based in the displacement of an element, such as a power cell holder, the power cell itself, a conductive metal cylinder or a metal sphere, until making contact with two electrical contacts which produces the closing of the circuit and the activation of the means of vibration.
or means based on an acceleration and/or position transducer of one or more axes and a programmable circuit that picks up the signals from the transducer, it analyzes them and generates the necessary signals for activating the vibrator at the right moment.

On the other side, the producing means of vibration can be an electric motor and an eccentric counterweight coupled thereto, or any other vibrating electro-mechanic device.

Also in a complementary or alternative manner, the device can contain an adjustable electronic circuit, with the purpose of progressively and automatically increasing the vibration power in the function of time.

In a possible embodiment, the device of the invention comprises a power cell holder for housing at least one power cell, which is provided with two axially opposed overhanging contacts or lugs, and the container box comprises some tilted structures with dielectric characteristics over which said power cell holder can roll through its lugs, and two electrical contacts wherein said tilted structures terminate, such that when the power cell holder comes to rest over said electrical contacts closes the motor circuit, in this way activating the vibrator.

The power cell holder for housing one power cell can directly be a power cell, which then is provided with the two axially opposed lugs.

In an embodiment, the tilted structures have a tilt between 35° and 90°.

The device of the invention can include, inside the container box, an adjustable timing electronic circuit, with the purpose of delaying the activation of the vibration.

The system of attachment of the device to the skull of the patient can be by means of a textile tape or it can be based on a single-use adhesive patch, with a socket for inserting the device, in this way improving the comfort of the patient and preventing maintenance and cleaning of the attaching strip.

The device can be attached to any other part of the human body besides the skull, with the purpose of preventing a specific position of that part of the body during sleep, in this way allowing relieving discomfort, pains or pathologies associated with a bad posture during sleep (e.g. recovery from surgical operations, hip or spinal column ailments, etc.).

The device, in a complementary embodiment, has memory for storing information relative to the patient and to the equipment, and connectivity for transmitting that information to an external device.

BRIEF DESCRIPTION OF THE DRAWINGS

For complementing the description to be carried out next, and with the object of helping to a better understanding of its characteristics, attached to the present specification, is a set of planes on which figures, in an illustrative and not limitative manner, the more significant details of the invention are depicted.

FIG. 1 is a perspective view of the device object of the invention can be observed.

FIG. 2A and FIG. 2B are a plant depiction of the device object of the invention is shown.

PREFERRED EMBODIMENT OF THE INVENTION

In view of the commented figures and of the applied numbering, a preferred embodiment although not limitative of the invention can be observed in the drawings, consisting of a container box (1) having a lid (3) over which there is a structure (4) for attaching a vibrating motor (10). Inside the box (1), a niche (5) is defined inside of which a vibrating motor (10) is arranged together with a counterweight (11), the vibrating motor (10) being fed with at least one power cell or battery housed in the power cell holder (14) arranged in the niche (6) of the box, wherein the power cell holder (14) has some overhanging contacts (15) as cylindrical lugs, with the purpose of being able to rotate over the tilted structures (7) if a tilting of the device is produced, until making contact with the contacts (8) of the circuit of the vibrating motor (10), closing the electrical circuit and thus bringing about the vibration of the mentioned device.

The detection sensitivity of the tilting of the device and the vibration will depend on the manufacturing angle of the tilted structures (7), since if said device stays in a side position, the rotary contacts (15) of the power cell holder (14) will manifest unbalance in the weight exercised by the power cell housed within it and due to the gravitational attraction, thus the power cell will roll in opposite direction to the contacts (8) of the niche (5) without closing the electrical circuit. The inverse effect is produced if a tilt is carried out heading for the supine decubitus position, which will roll the power cell until making contact with the mentioned contacts (8) closing the electrical circuit and producing a warning vibration, thus, if there was a 90° angle, the maximum sensitivity for the assembly would be established, the optimum one resulting from some 35°, with the purpose of creating a tolerance margin to the movement without activating the device.

The explained embodiment is one among the possible embodiments, since instead of a power cell holder with end lugs, a conductive metal cylinder, or the power cell itself can be employed as equivalent means. Instead of a motor with an eccentric, equivalent means can be employed such as any other vibrating electro-mechanic device, since in any case they produce the desired effect, being evident the substitution of one for another. Instead of carrying out the attachment to the skull, it could be carried out to any other part of the body, since it is an equivalent embodiment that does not alter the looked-for results.

Additionally, the device object of the invention can have a programmable delay circuit which allows selecting the delay in the activation of the means of vibration.

Also in a complementary or alternative manner, the device can contain an adjustable electronic circuit, with the purpose of progressively and automatically increasing the vibration power in the function of time.

The device in a complementary embodiment has memory for storing information relative to the patient and to the equipment and connectivity for transmitting that information to an external device.

The system of attachment of the device to the skull of the patient can be by means of a textile tape or can be based in a single-use adhesive patch, with a socket for inserting the device, in this way improving the comfort of the patient and preventing maintenance and cleaning of the attaching strip.

The model in its essentiality can be implemented in other embodiments which would differ in detail by way of example in the description and which will equally reach the protection asked for. So, it can be manufactured in any shape, size and with the most suitable materials as all of this is in the spirit of what is claimed.

What is claimed is:

1. A cranial device with rotary tilt sensor, the cranial device comprising
   a container box configured to attach to the skull of sleeping person,
   an electrical motor housed inside the container box,
   an eccentric counterweight coupled to the electrical motor to form a vibrator,
   a power cell holder housing at least one power cell, the power cell including two axially opposed overhanging contacts,
   wherein the container box includes at least two tilted structures with dielectric characteristics over which the power cell holder can roll supported on the overhanging contacts, and two electrical contacts, and wherein the tilted structures terminate
   so that when the power cell holder comes to rest over the two electrical contacts the at least one power cell is electrically connected with the electrical motor to activate the vibrator.

2. The cranial device with rotary tilt sensor of claim 1, wherein the power cell holder is the power cell.

3. The cranial device with rotary tilt sensor of claim 1, wherein the tilted structures have a tilt of between about 35° and about 90°.

4. The cranial device with rotary tilt sensor of claim 1, wherein the container box houses an adjustable timing electronic circuit configured to delay activation of the vibrator.

5. The cranial device of claim 1, wherein the container box houses an adjustable electronic circuit configured for progressively and automatically increasing the vibration power in the function of time.

6. The cranial device of claim 1, further comprising a textile tape configured to attach the container box to the skull of the sleeper.

7. The cranial device of claim 1, further comprisng an adhesive patch with a socket for inserting the container box, the adhesive patch configured to attach the container box to the skull of the sleeper.

8. The cranial device of claim 1, further comprising a memory configured for storing information relative to the patient and to the equipment, and configured to provide connectivity for transmitting the information to an external device.

* * * * *